United States Patent
Wang et al.

(10) Patent No.: US 8,048,361 B2
(45) Date of Patent: Nov. 1, 2011

(54) METHOD FOR FORMING POROUS BIO-MIMICKING SCAFFOLD

(75) Inventors: De-Yao Wang, Taipei (TW); Lee-Lee Chang, Taipei (TW); Yi-You Huang, Taipei (TW)

(73) Assignee: National Taiwan University, Taipei (TW)

( * ) Notice: Subject to any disclaimer, the term of this patent is extended or adjusted under 35 U.S.C. 154(b) by 84 days.

(21) Appl. No.: 12/123,962

(22) Filed: May 20, 2008

(65) Prior Publication Data
US 2009/0289387 A1    Nov. 26, 2009

(51) Int. Cl.
*B29C 44/04* (2006.01)
(52) U.S. Cl. .................................................. 264/465
(58) Field of Classification Search ............. 264/465
See application file for complete search history.

(56) References Cited

U.S. PATENT DOCUMENTS

| | | | | |
|---|---|---|---|---|
| 7,661,541 B2 * | 2/2010 | Dao et al. | | 210/500.22 |
| 2002/0081732 A1 * | 6/2002 | Bowlin et al. | | 435/446 |
| 2004/0124146 A1 * | 7/2004 | Dao et al. | | 210/645 |
| 2004/0241436 A1 * | 12/2004 | Hsieh et al. | | 428/361 |
| 2006/0204441 A1 * | 9/2006 | Atala et al. | | 424/9.6 |
| 2006/0228435 A1 * | 10/2006 | Andrady et al. | | 425/174.8 R |
| 2006/0246121 A1 * | 11/2006 | Ma et al. | | 424/443 |
| 2006/0261005 A1 * | 11/2006 | Dao et al. | | 210/505 |
| 2009/0074832 A1 * | 3/2009 | Zussman et al. | | 424/423 |
| 2009/0127748 A1 * | 5/2009 | Takahashi | | 264/465 |
| 2009/0152773 A1 * | 6/2009 | Barinov et al. | | 264/465 |

FOREIGN PATENT DOCUMENTS
WO    WO 2007 079488    *    7/2007

* cited by examiner

*Primary Examiner* — Joseph Del Sole
*Assistant Examiner* — Kimberly A Stewart
(74) *Attorney, Agent, or Firm* — WPAT, PC; Justin King (57) ABSTRACT

The present invention discloses a method for forming a porous bio-mimicking scaffold. At first, at least two types of solutions are provided where at least one of the solutions is a bio-mimicking scaffold solution comprising a bio-mimicking scaffold and at least one of the solutions is a pore forming solution comprising a pore forming material having at least one corresponding specific solvent. Then, a filling process is performed to fill the solutions into different needles of a blending injection device. Following that, an electrospinning process is performed to form a composite material. Each material type for forming the composite material is selected from the group consisting of the following: fiber, particle, and combination of fiber and particle. Finally, a removing process using the solvent to dissolve the pore forming material is performed to thereby form a porous bio-mimicking scaffold.

16 Claims, 15 Drawing Sheets

METHOD FOR FORMING POROUS BIO-MIMICKING SCAFFOLD

BACKGROUND OF THE INVENTION

1. Field of the Invention

The present invention is generally related to a method for forming a bio-mimicking scaffold, and more particularly to a method for forming a porous bio-mimicking scaffold.

2. Description of the Prior Art

Electrospinning is one of techniques to produce nanofibers. The principle of electrospinning is to utilize a material solution under high voltage. When the charge repulsion force generated by the charges accumulated on the surface of the solution is larger than the surface tension, a Taylor cone is formed on the surface of the solution. The cone tip exceeds the tension to emit nanofibers toward a collecting plate with an opposite electric property. Different collecting plates can be used to collect nanofibers in different directions.

Generally, the diameter of nanofibers is about 0.01 times the diameter of common fibers. In one gram of fibers with a diameter of 50 nm, the total surface area is about 1,000 $m^2$. Since nanofibers have tremendous surface area and high porosity, they have many special applications. Traditionally, the material of nanofibers is carbon fibrils, man-made polymeric fiber, or alumina fiber, etc.

Electrospinning nanofibers having high strength and high surface area can be utilized to fabricate cloth with special functions, such as chemical resistant, water-proof and breathable, anti-staining, and so forth. In textile industry, nanofibers have great market. Nano-Tex Co. has developed and commercialized products made of nanofibers. Nanofibers are also considered as scaffolds for filtration and medical tissue engineering. In addition, they have potential in the applications of transporting media for medicine, sensors, nano-electronics, etc.

Besides, in the biotechnology application of nanofibers, there are reports in discussing the interaction between nanofibers and cells. Elias et al implant human osteoblasts into scaffolds comprised by nanofibers with different dimensions to perform culture in vitro. After performing culture for 3 weeks, cell growth is in a good condition and alkaline phosphatase activity and calcium concentration secreted by the osteoblasts are increased with the increase of the culture time.

Yoshimoto et al implant mesenchymal stem cells into scaffolds comprised by poly caprolactone (PCl) nanofibers to perform culture by a dynamic bio-reactor. After performing culture for 4 weeks, it is found that not only cell-polymer constructs maintain the original dimension and shape but also cell laminated proliferation and the growth of cell matrix for the cells in the constructs are observed by SEM. In addition, it is found from the immunohistochemical staining method that type I collagen is formed. Therefore, in light of the above results, it shows that nanofibers can aid cell growth.

However, if nanofibers are piled up tightly and have low porosity, cell growth and differentiation will be affected. Christopher et al have found that cow endothelial cells grow on bio-matrix with a small pore diameter (<100 μm) and have higher apoptosis probability. Thus, a novel method for preparing a porous bio-mimicking scaffold is needed to provide a bio-mimicking scaffold with a proper pore diameter and appropriate porosity.

SUMMARY OF THE INVENTION

In light of the above mentioned background, in order to fulfill the requirements of the industry, the present invention provides a method for forming a porous bio-mimicking scaffold.

One object of the present invention is to simultaneously prepare micro/nano-fibers for multiple materials by the improved electrospinning technique and to control the dimension of the prepared fibers so as to mimic natural extracellular matrix. Polymeric micro/nano-fibers and particles can also be simultaneously prepared and deposited and then a specific composition is dissolved and removed to provide porous space for cell culture. Therefore, the invention can provide a bio-mimicking scaffold with proper porosity.

Another object of the present invention is to utilize the direct and economical improved electrospinning technique to quickly and massively produce and blend micro- and nano-polymeric fibers/particles/combination of fibers and particles. Therefore, this present invention does have the economic advantages for industrial applications.

Accordingly, the present invention discloses a method for forming a porous bio-mimicking scaffold. At first, at least two types of solutions are provided where at least one of the solutions is a bio-mimicking scaffold solution comprising a bio-mimicking scaffold and at least one of the solutions is a pore forming solution comprising a pore forming material having at least one corresponding specific solvent. Then, a filling process is performed to fill the solutions into different needles of a blending injection device.

Following that, a first electric property is applied to the blending injection device and a second electric property is applied to a collecting device. The first electric property is opposite to the second electric property. A potential difference exists between the blending injection device and the collecting device. Furthermore, an electrospinning process is performed to have the solutions emitted from the needles of the blending injection device toward the collecting device so as to form a composite material on the collecting device. Each material type for forming the composite material is selected from the group consisting of the following: fiber, particle, and combination of fiber and particle. Finally, a removing process using the solvent to dissolve the pore forming material to remove the pore forming material is performed to thereby form a porous bio-mimicking scaffold.

BRIEF DESCRIPTION OF THE DRAWINGS

FIGS. 2B1~2B4 are scanning electron microscope (SEM) images of bio-mimicking scaffolds by blending gelatin fibers/particles/combination of both with different concentration;

FIGS. 2C1~2C4 are scanning electron microscope (SEM) images of bio-mimicking scaffolds by blending poly caprolactone-co-lactic acid (PCL) fibers/particles/combination of both with different concentration;

DESCRIPTION OF THE PREFERRED EMBODIMENTS

What is probed into the invention is a method for forming a porous bio-mimicking scaffold. Detail descriptions of the steps and compositions will be provided in the following in order to make the invention thoroughly understood. Obviously, the application of the invention is not confined to specific details familiar to those who are skilled in the art. On the other hand, the common steps and compositions that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

In one embodiment of the present invention, a method for forming a porous bio-mimicking scaffold is provided. At first, at least two types of solutions are provided where at least one of the solutions is a bio-mimicking scaffold solution comprising a bio-mimicking scaffold and at least one of the solutions is a pore forming solution comprising a pore forming material having at least one corresponding specific solvent. The bio-mimicking scaffold and the pore forming material are independently selected from the group consisting of the following or any combination thereof: chitosan, poly lactic acid, poly caprolactone-co-lactic acid, collagen, polyamide, and gelatin. Then, a filling process is performed to fill the solutions into different needles of a blending injection device.

After the filling process is completed, a first electric property is applied to the blending injection device and a second electric property is applied to a collecting device. The first electric property is opposite to the second electric property. A potential difference exists between the blending injection device and the collecting device. The distance between the blending injection device and the collecting device is defined as an electric field distance. The electric field distance divided by the potential difference is electric field intensity (V/m). Furthermore, an electrospinning process is performed to have the solutions emitted from the needles of the blending injection device toward the collecting device so as to form a composite material on the collecting device.

The solutions are repeatedly emitted from different needles of the blending injection device toward the collecting device according to a specific order or sequentially. As shown in FIG. 1A, FIG. 1B, FIG. 1C, and FIG. 1D, each material type for forming the composite material is selected from the group consisting of the following: fiber, particle, and combination of fiber and particle, where the diameter of particles is about 1,000 nm ~200,000 nm and the diameter of fibers is about 10 nm ~2,000 nm.

After the electrospinning process is completed, a removing process using the solvent to dissolve the pore forming material to remove the pore forming material is performed to thereby form a porous bio-mimicking scaffold. The solvent is selected from the group consisting of the following or any combination thereof: acetone and 1,4-dioxane. In addition, the porous bio-mimicking scaffold has a pore diameter within about 10 nm ~200,000 nm.

The blending injection device can comprise an injection flow controller to control the flow within about 0.1~10 ml/hr. The blending injection device can be a spinning-type or oscillating-type blending injection device. The spinning-type blending injection device comprises a spinning speed controller to control the flow within about 100~10,000 rpm. On the other hand, the oscillating-type blending injection device comprises an oscillating speed controller to control the flow within about 100~1,000 mm/min.

The collecting device can be a roller-type or plate-type collecting device. The roller-type collecting device comprises a roller collecting speed controller to control the collecting speed within about 0~10,000 rpm. On the other hand, the plate-type collecting device comprises a plate collecting controller to control the collecting speed within about 0~1,000 mm/min.

The type of each material component included in the composite material is related to the concentration of the corresponding solution. In the bio-mimicking scaffold solution, the higher is the content of the bio-mimicking scaffold, the type of the formed material via the electrospinning process is closer to a fiber. On the contrary, the lower is the content of the bio-mimicking scaffold, the type of the formed material via the electrospinning process is closer to a particle. Besides, in the pore forming solution, the higher is the content of the pore forming material, the type of the formed material via the electrospinning process is closer to a fiber. On the contrary, the lower is the content of the pore forming material, the type of the formed material via the electrospinning process is closer to a particle.

The type of each material component included in the composite material is related to the electric field intensity (V/m). In the bio-mimicking scaffold solution, the higher is the voltage difference; the type of the formed material via the electrospinning process is closer to a fiber. On the contrary, the lower is the voltage difference; the type of the formed material via the electrospinning process is closer to a particle. On the other hand, in the pore forming solution, the higher is the voltage difference; the type of the formed material via the electrospinning process is closer to a fiber. On the contrary, the lower is the voltage difference; the type of the formed material via the electrospinning process is closer to a particle.

On the other hand, except the above factors to change the composite material type, the following factors also have effects on the composite material type: (1) the feeding rate of the polymer; (2) the properties of the polymer, including viscosity, molecular weight, conductivity, solvent type, and additive; (3) the diameter of the needle; (4) the distance between the needle and the collecting device; and (5) the atmosphere condition.

In a preferred example, a crosslinking process can be carried out after the electrospinning process and before the removing process. The crosslinking process uses a crosslinking reagent to have the chosen material undergo crosslinking. The crosslinking reagent is selected from the group consisting of the following or any combination thereof: glutaraldehyde and formaldehyde.

In the prior electrospinning technique, the particle type formed by low electric intensity or low material concentration is considered to be failed technically. This characteristic has not been applied in fabricating a composite material. The invention conquers the technical bias by those who are skilled in the art and uses such discarded technique and improves it to solve the problem in the prior art. Thus, the invention can not be easily achieved.

Example 1

The improved electrospinning apparatus, used in the method for forming a porous bio-mimicking scaffold, comprises an electrically conductive blending injection device, an injection flow controller, a blending speed controller, an electrically conductive collecting device, a collecting speed controller, a high voltage supplying device, and other auxiliary devices. The electrically conductive blending injection device can be loaded with at least two sets of needles and have at least two outlets for preparing micro- and nano-fibers and particles of at least two materials.

The blending method can be of oscillating or spinning type. The spinning type blending has a spinning speed of 100~10,000 rpm. The injection flow is controlled within 0.1~10 ml/hr. The electrically conductive collecting device can be of plate, roller, multi-electrode type, etc. The collecting speed by the roller-type is controlled within 0~10,000 rpm. The high voltage supplying device generates 0.1~30 kV. The improved electrospinning apparatus can simultaneously prepare and blend micro- and nano-polymeric fibers and particles of two materials.

Figure 1A:
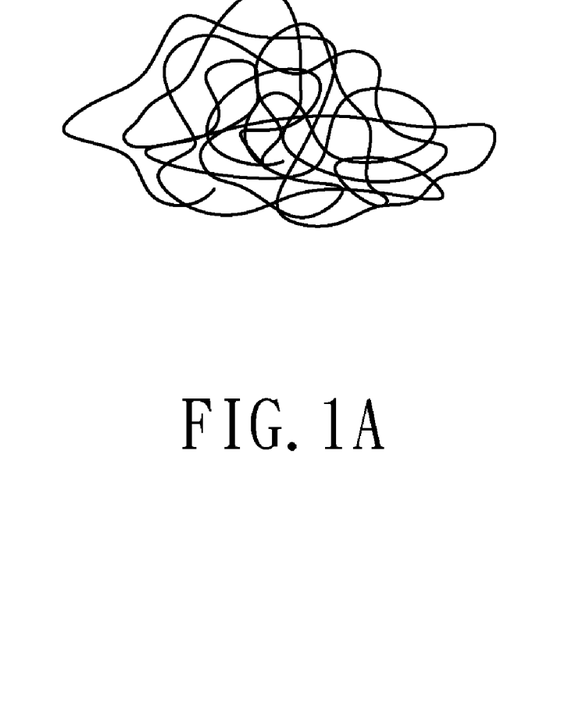
FIGS. 1A~1D show schematic diagrams illustrating every material type for forming the composite material according to the invention.
Figure 1B:
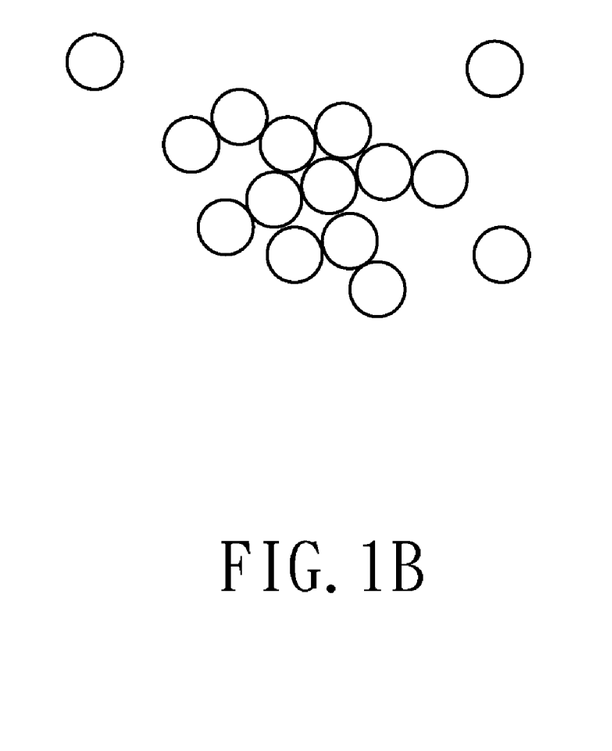
Figure 1C:
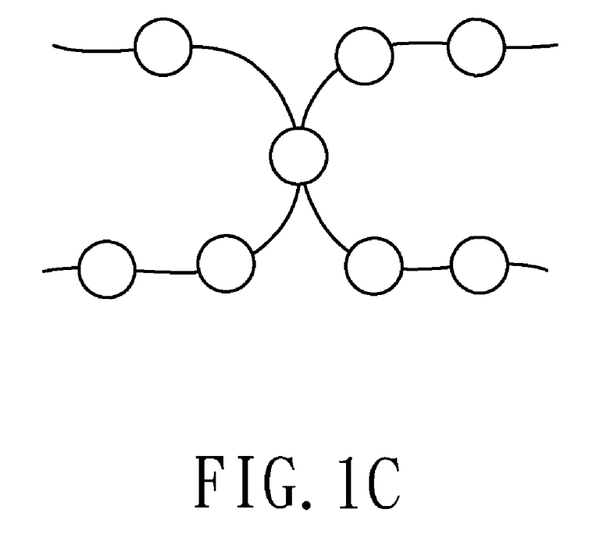
Figure 1D:
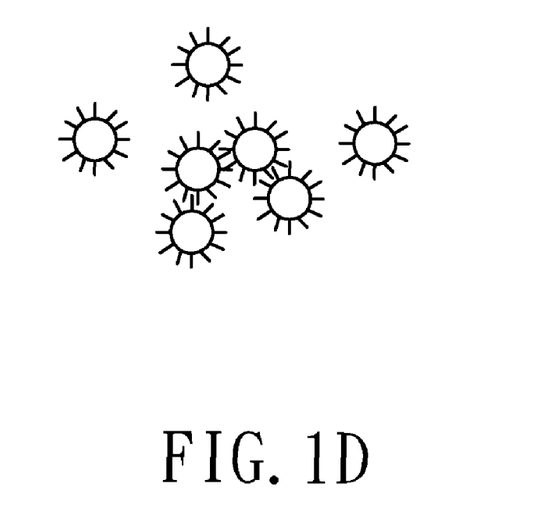
Figure 2A:
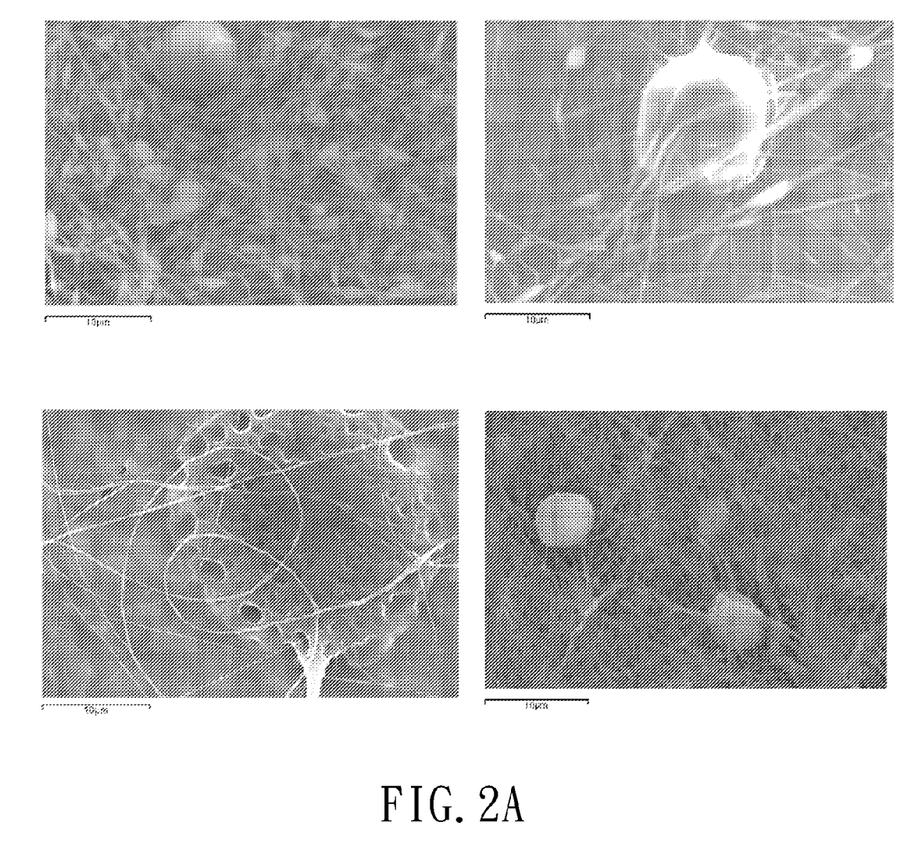
FIG. 2A is a scanning electron microscope (SEM) image of a bio-mimicking scaffold by blending gelatin and poly caprolactone-co-lactic acid (PCL) particles.
Figure 2B:
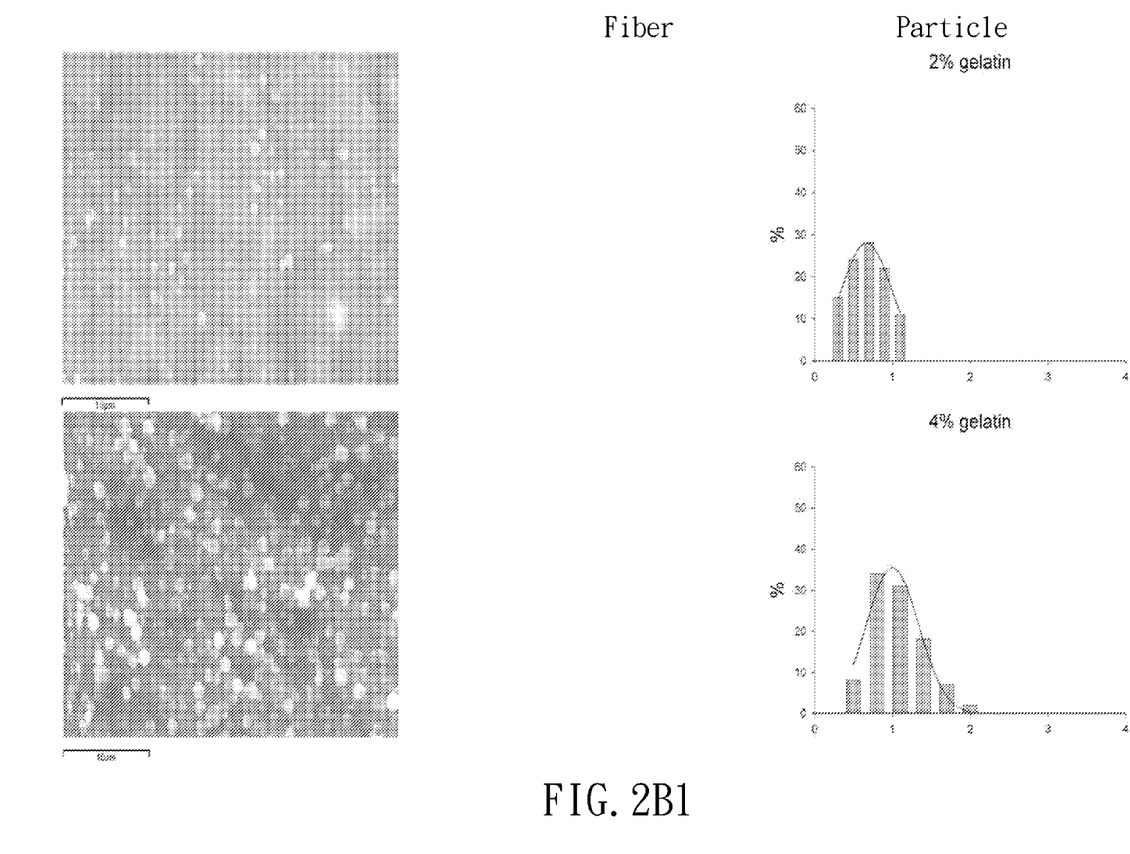
Figure 2B:
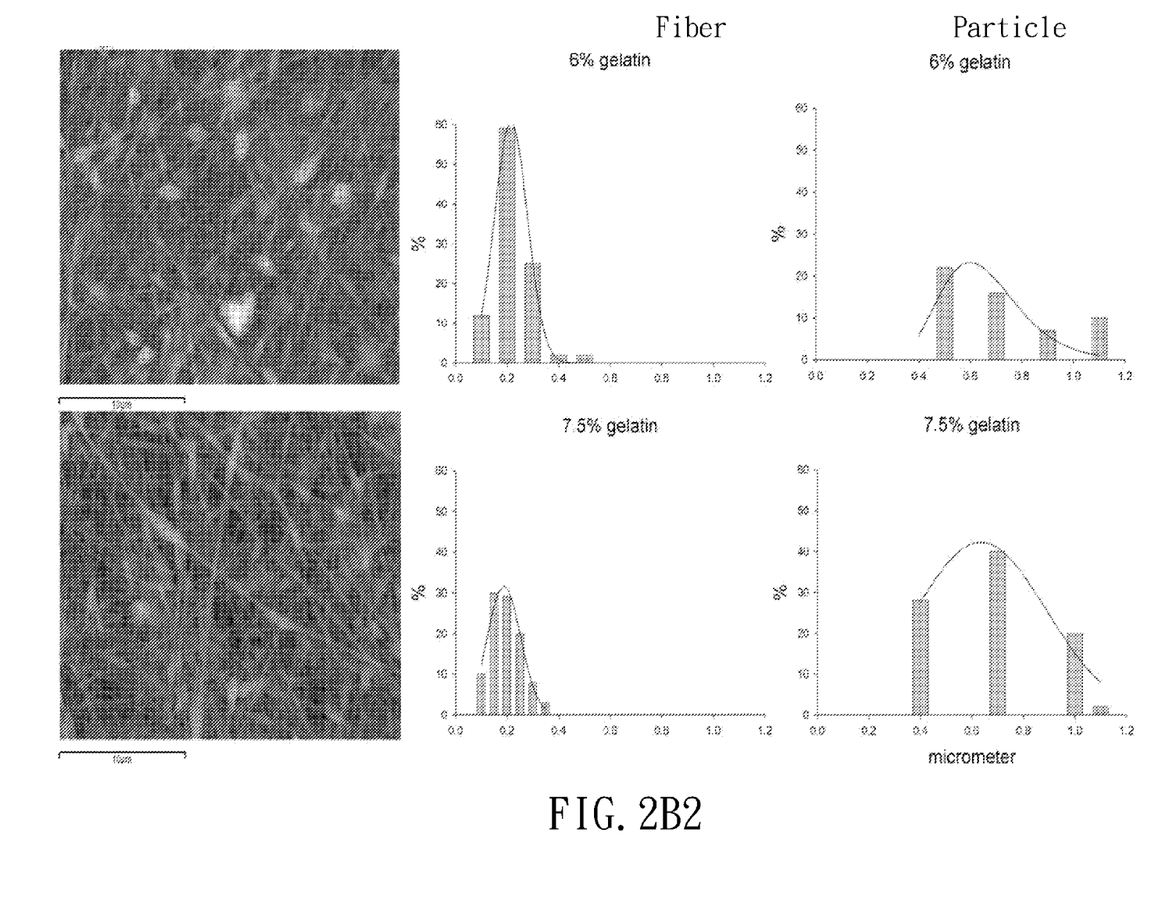
Figure 2B:
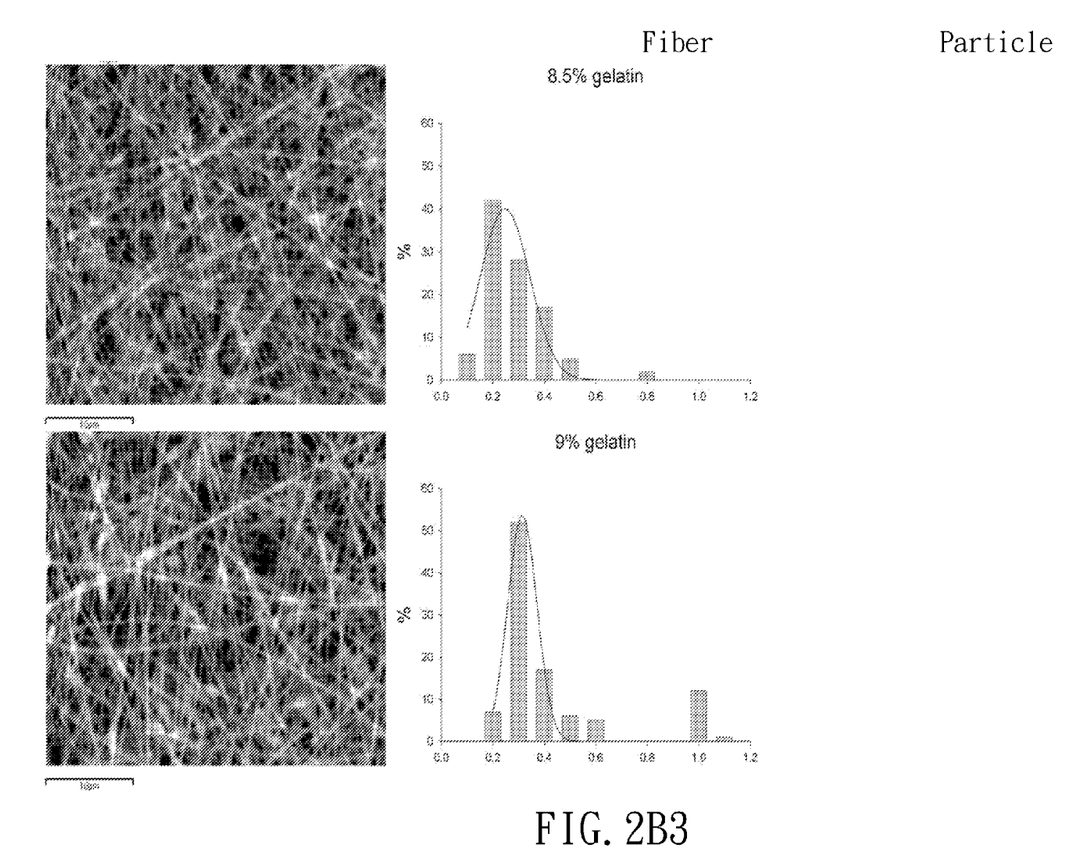
Figure 2B:
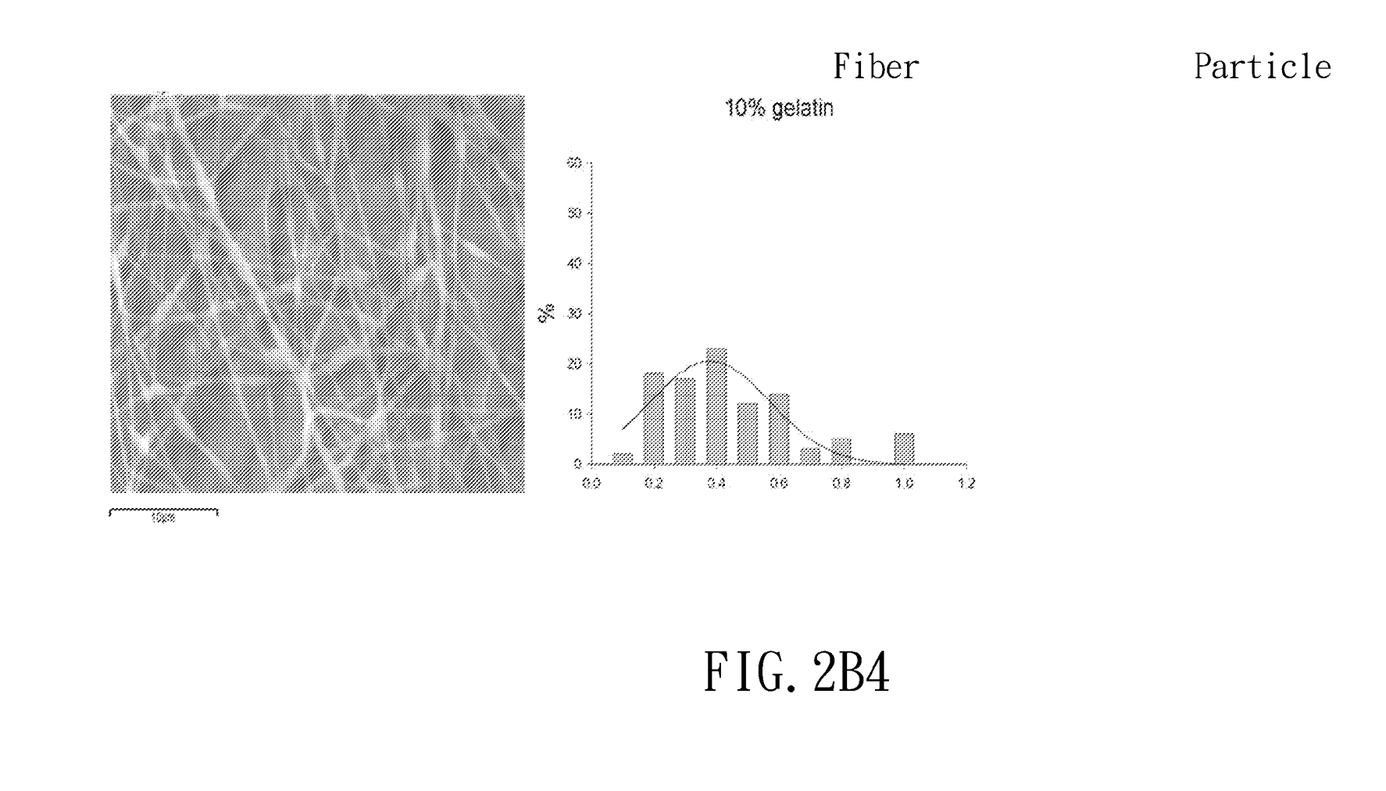
Figure 2C:
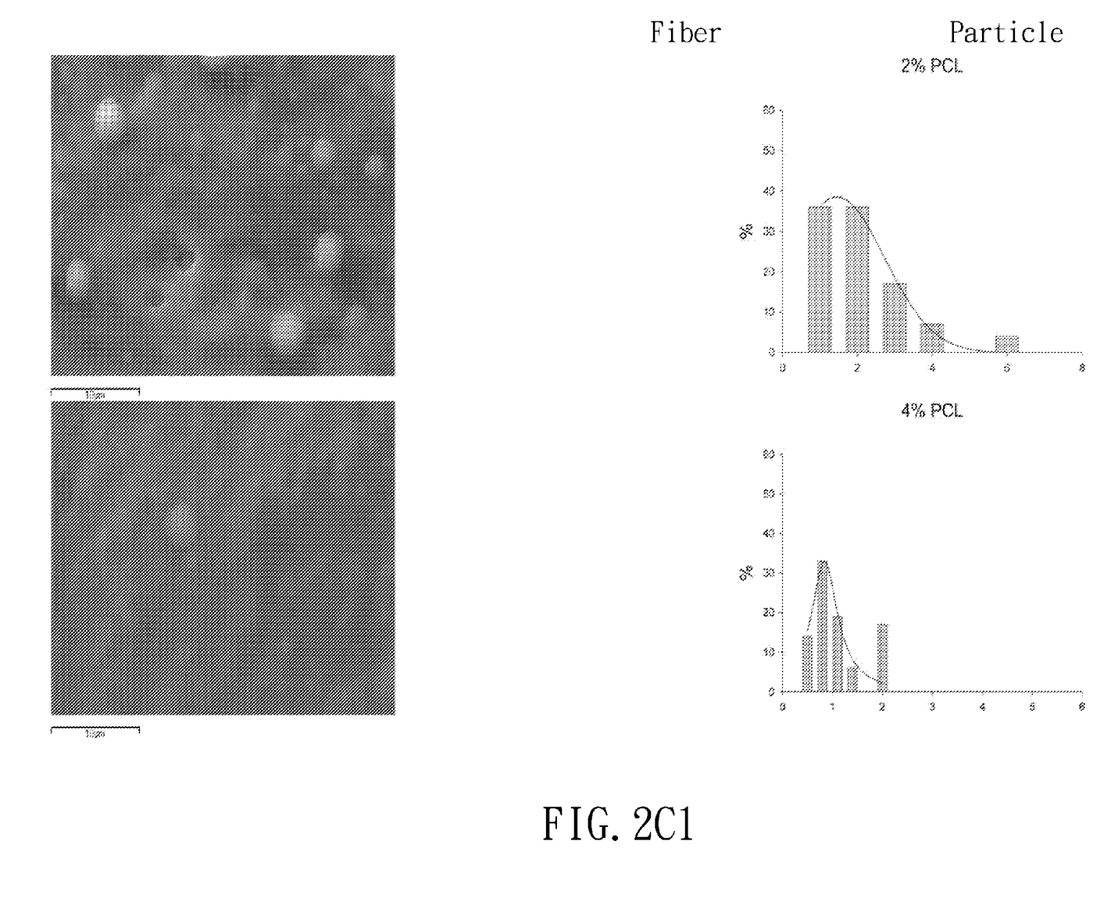
Figure 2C:
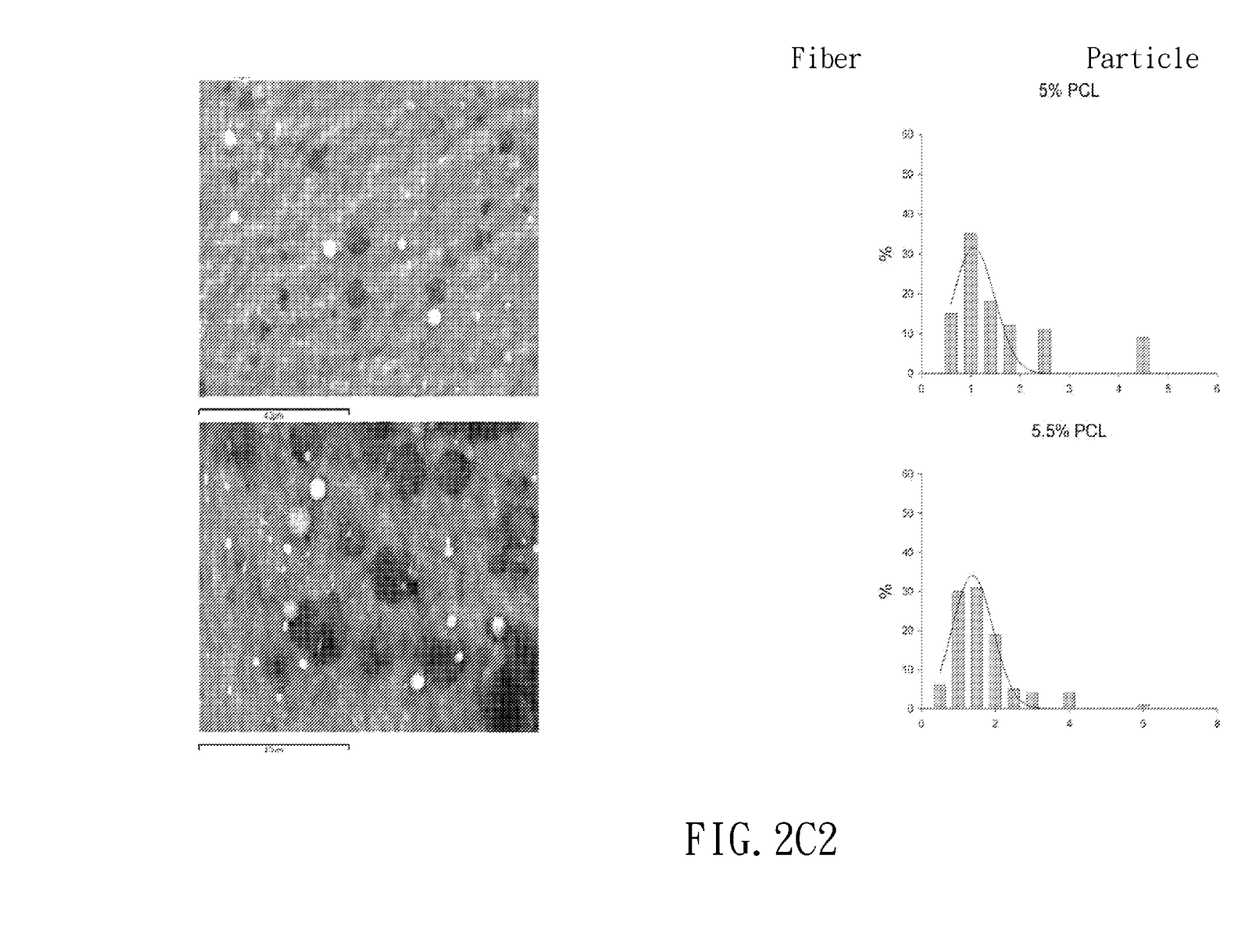
Figure 2C:
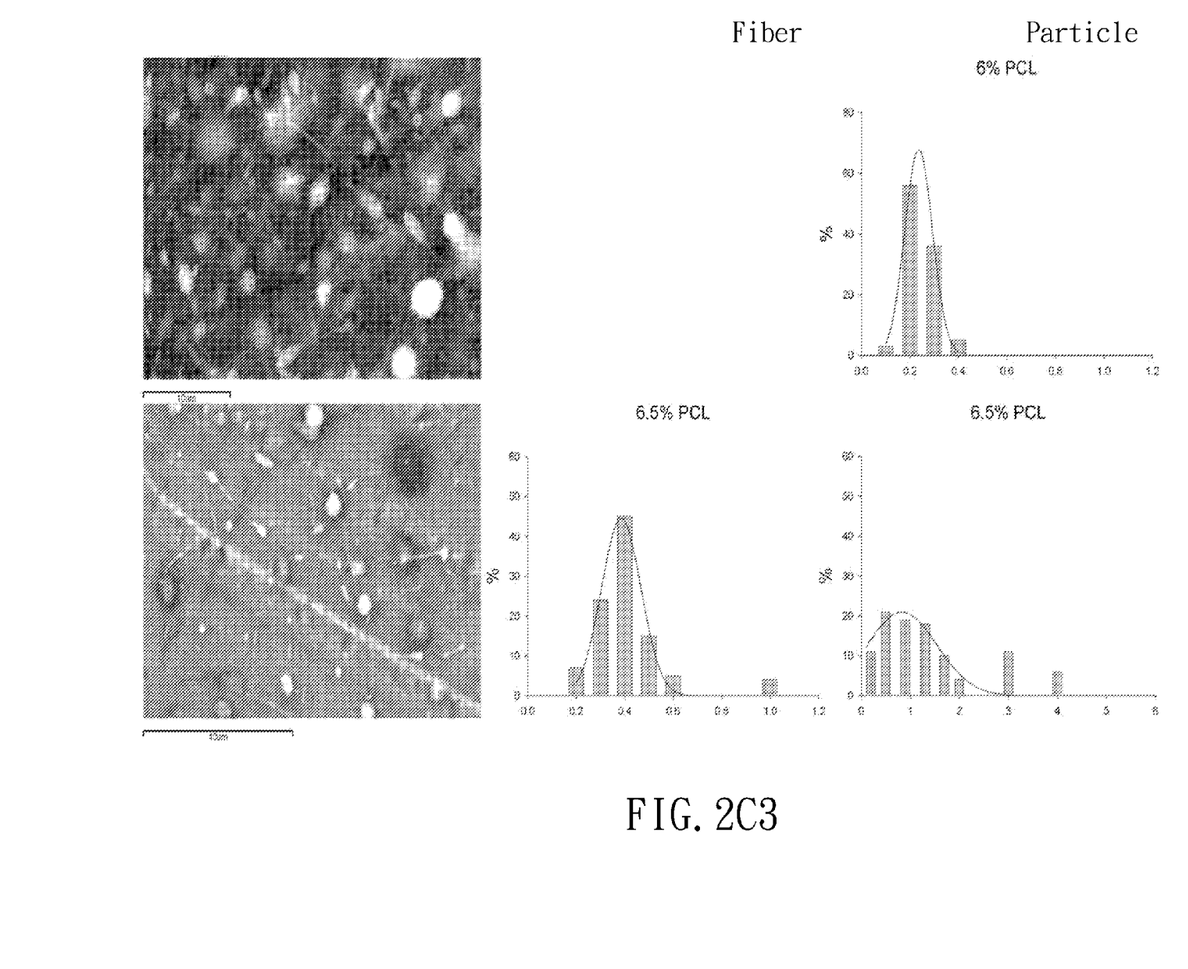
Figure 2C:
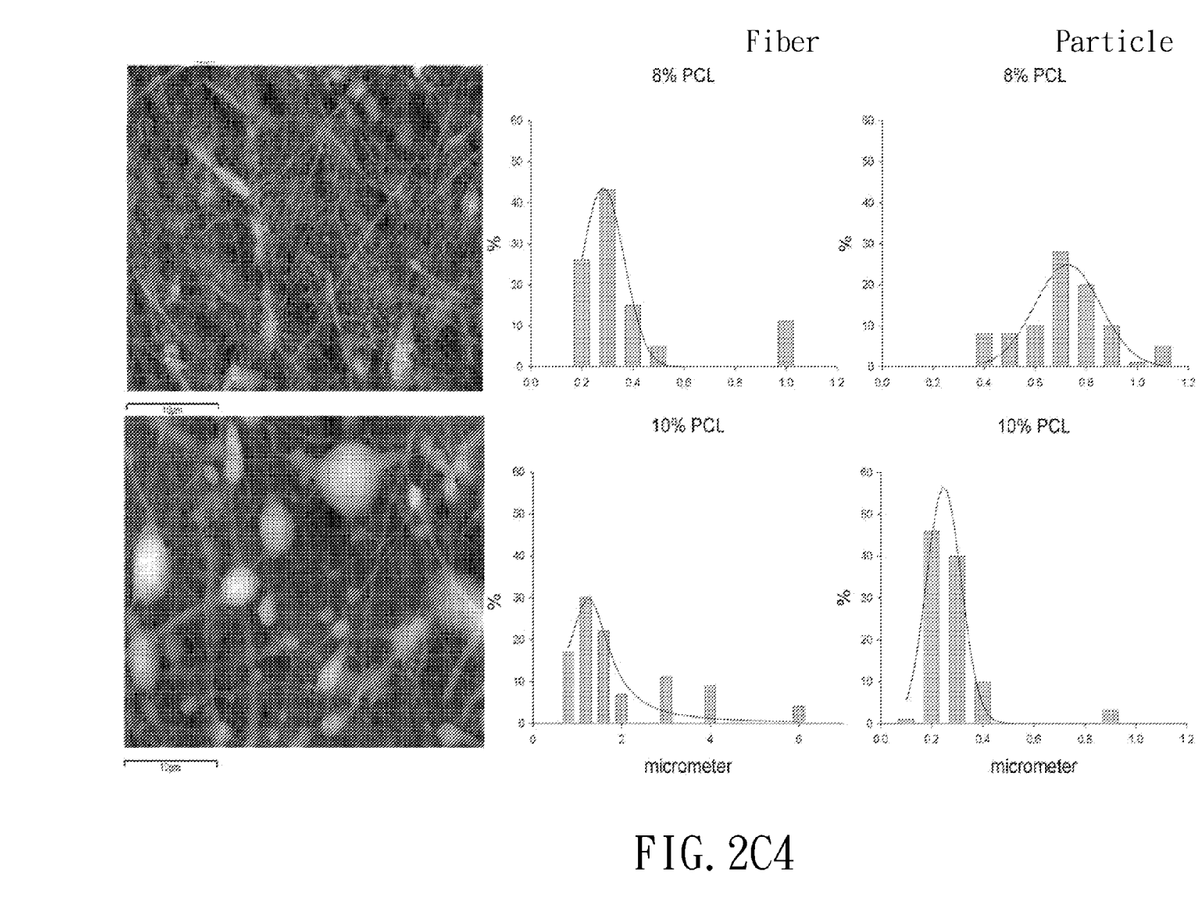

As shown in FIG. 2A, 2%~15% of poly caprolactone-co-lactic acid (PCL) is used and, in FIG. 2B, 2%~12% of gelatin is used. Both are filled in the needles of the electrically conductive blending injection device, separately. The two micro- and nano-polymeric fibers and micro- and nano-polymeric particles are blended under the conditions of 9 kV, 0 ml/hr, a spinning collecting speed of 2,000 rpm, and the distance between the electrically conductive blending injection device and the collecting plate being 3 mm.

The blended micro- and nano-polymeric fibers and particles undergo crosslinking reaction and partial dissolving treatment. Gelatin fibers with a diameter of 10~2,000 nm together with 0.5-8% glutaraldehyde vapor undergo crosslinking for 1-2 days, with the gelatin acting as the bio-mimicking scaffold. Then, acetone is used to dissolve the PCL particles with a diameter of 1,000-200,000 nm, with the PCL acting as the pore forming material. The porous space is formed after dissolution so as to form a bio-mimicking scaffold with appropriate porosity. The prepared material is placed in DMEM+10% FBS and placed in the environment of 37° C., 5% $CO_2$ cell culture for performing the decomposition speed test. It is also planted with fibroblasts having density of $10^5$ cells/cm$^2$ to perform the cell survival rate and bio-compatibility tests. The subsequent application characteristic of the bio-mimicking scaffold is evaluated from these tests.

As shown in FIGS. 2B1~2B4, the bio-mimicking scaffolds having fibers and particles are formed by different concentration of gelatin. As the concentration of gelatin is between 2~4%, the type of the formed bio-mimicking scaffold is closer to a particle. As the concentration of gelatin is 6~7.5%, the type of the formed bio-mimicking scaffold is combination of fiber and particle. As the concentration of gelatin is between 8.5~10%, the type of the formed bio-mimicking scaffold is closer to a fiber.

As shown in FIGS. 2C1~2C4, the bio-mimicking scaffolds having fibers and particles are formed by different concentration of poly caprolactone-co-lactic acid (PCL). As the concentration of PCL is between 2~6%, the type of the formed bio-mimicking scaffold is closer to a particles. As the concentration of PCL is between 6.5~10%, the type of the formed bio-mimicking scaffold is closer to combination of fiber and particle.

Figure 3:
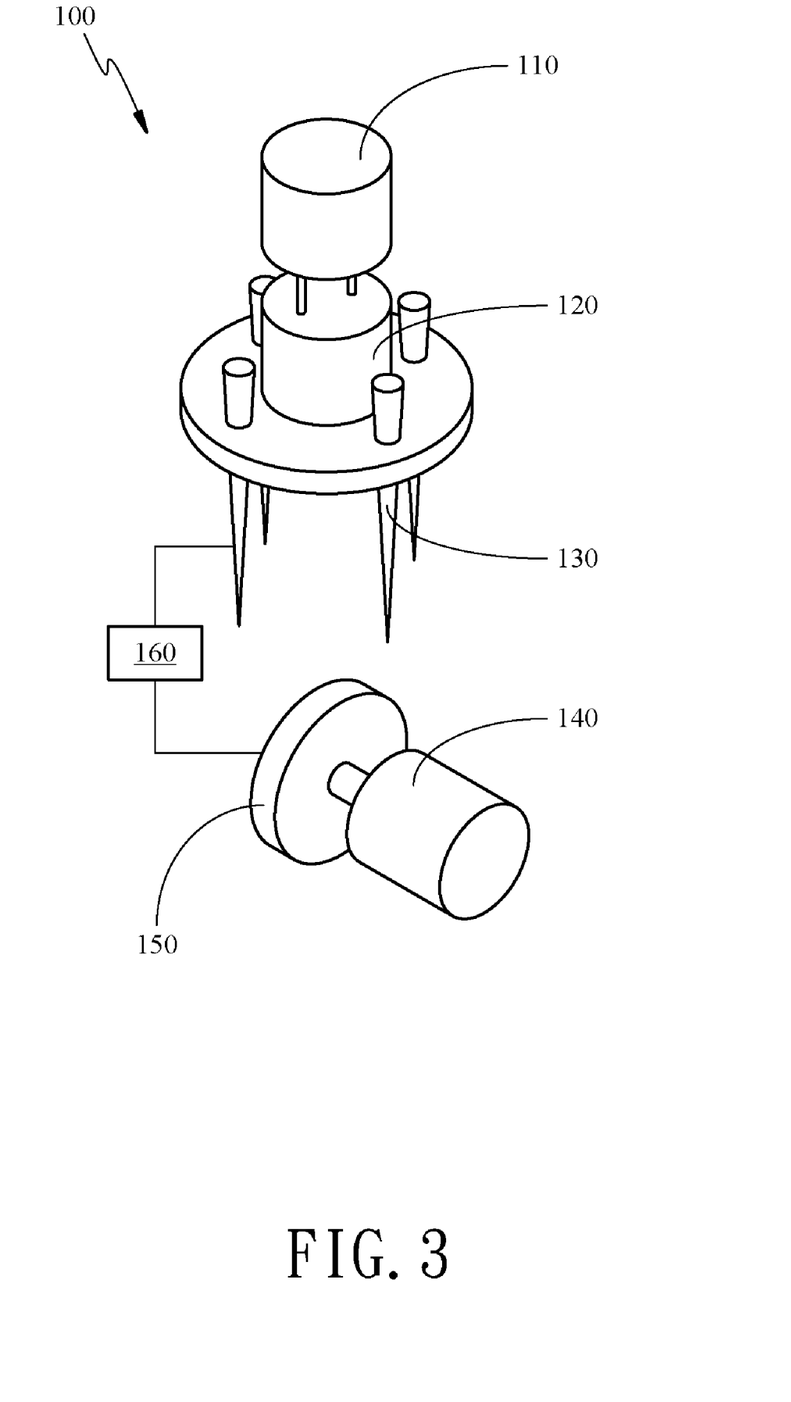
FIG. 3 shows a schematic diagram illustrating the spinning-type blending injection device combined with a roller-type collecting device according to the present invention.

As shown in FIG. 3, the spinning-type blending injection device combined with a roller-type collecting device 100 comprises: a blending speed controller 110, a spinning-type electrically conductive blending injection device 120, a needle 130, a collecting speed controller 140, a roller-type collecting device 150, and a high voltage supplying device and other auxiliary devices 160.

Figure 4:
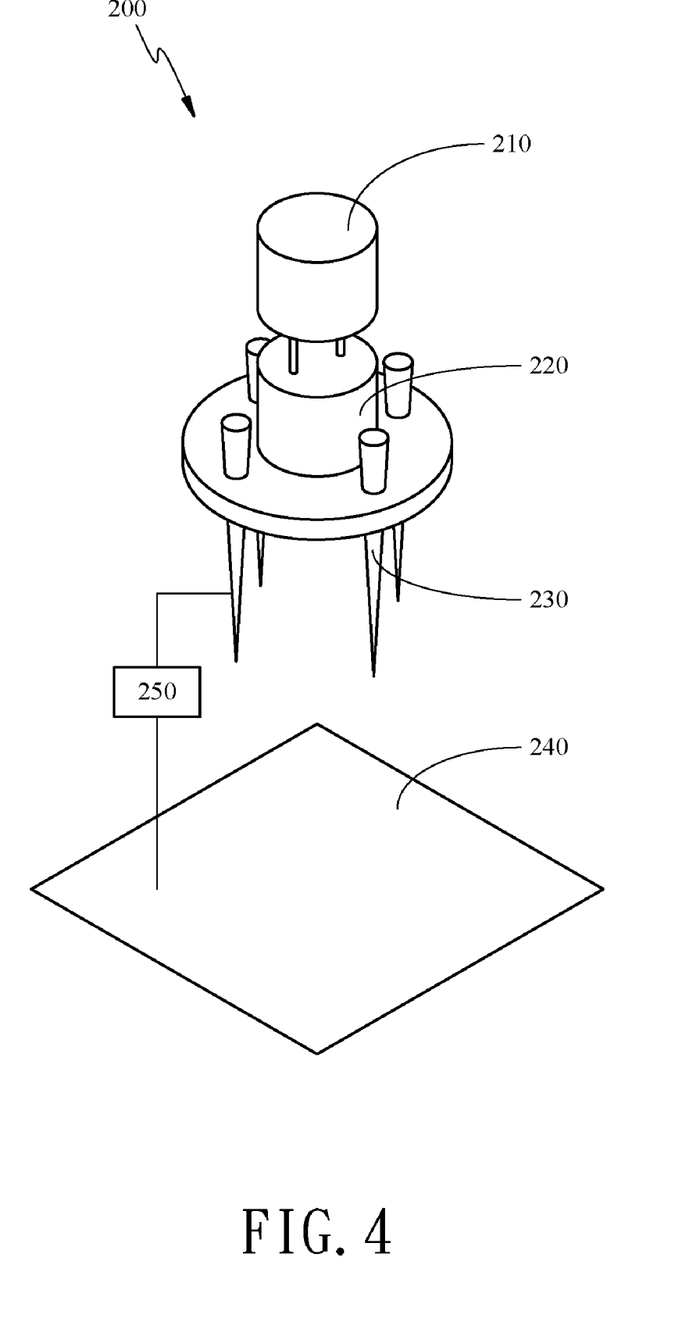
FIG. 4 shows a schematic diagram illustrating the spinning-type blending injection device combined with a plate-type collecting device according to the present invention.

As shown in FIG. 4, the spinning-type blending injection device combined with a plate-type collecting device 200 comprise: a blending speed controller 210, a spinning-type electrically conductive blending injection device 220, a needle 230, a plate-type collecting device 240, and a high voltage supplying device and other auxiliary devices 250.

Figure 5:
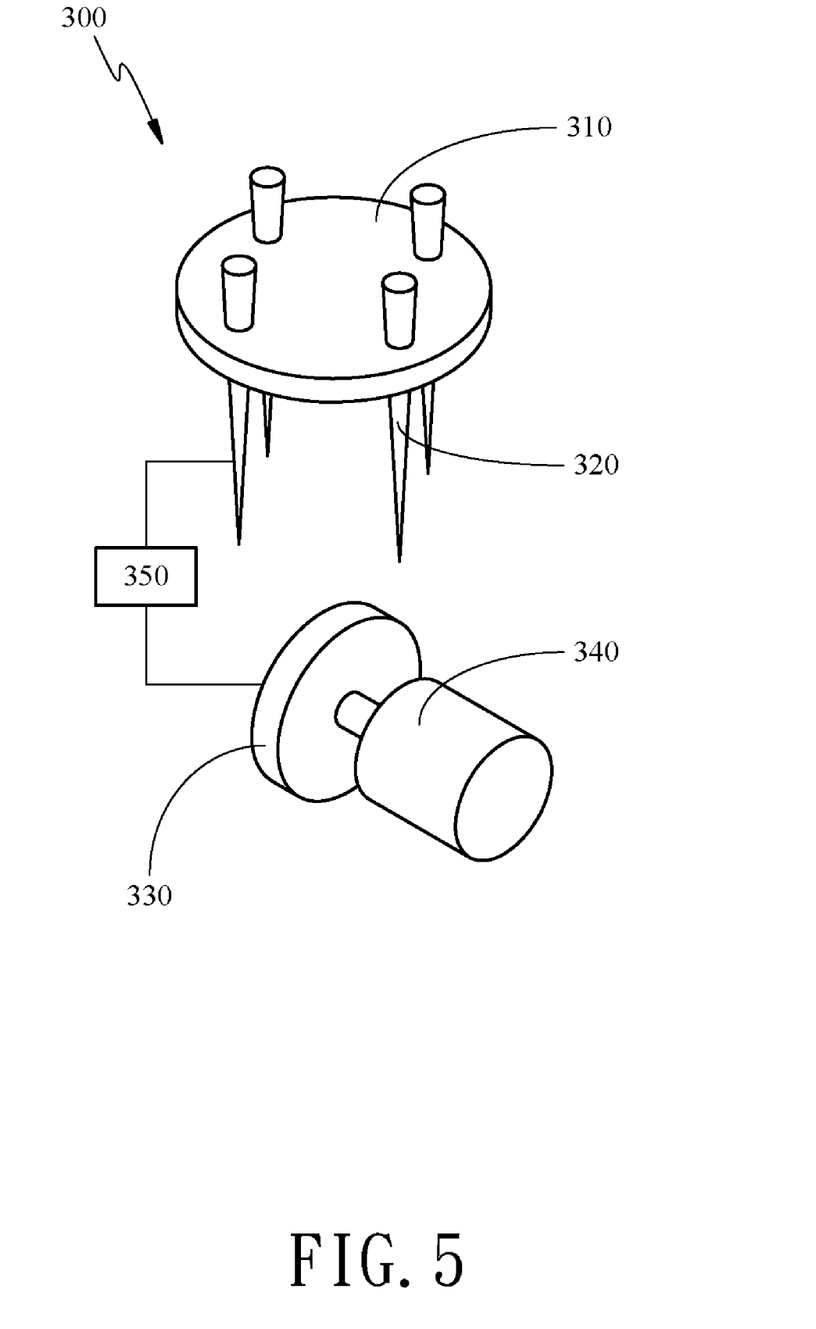
FIG. 5 shows a schematic diagram illustrating the oscillating-type blending injection device combined with a roller-type collecting device according to the present invention.

As shown in FIG. 5, the oscillating-type blending injection device combined with a roller-type collecting device 300 comprises: an oscillating-type blending injection device 310, a needle 320, a roller-type collecting device 330, a collecting speed controller 340, and a high voltage supplying device and other auxiliary devices 350.

Figure 6:
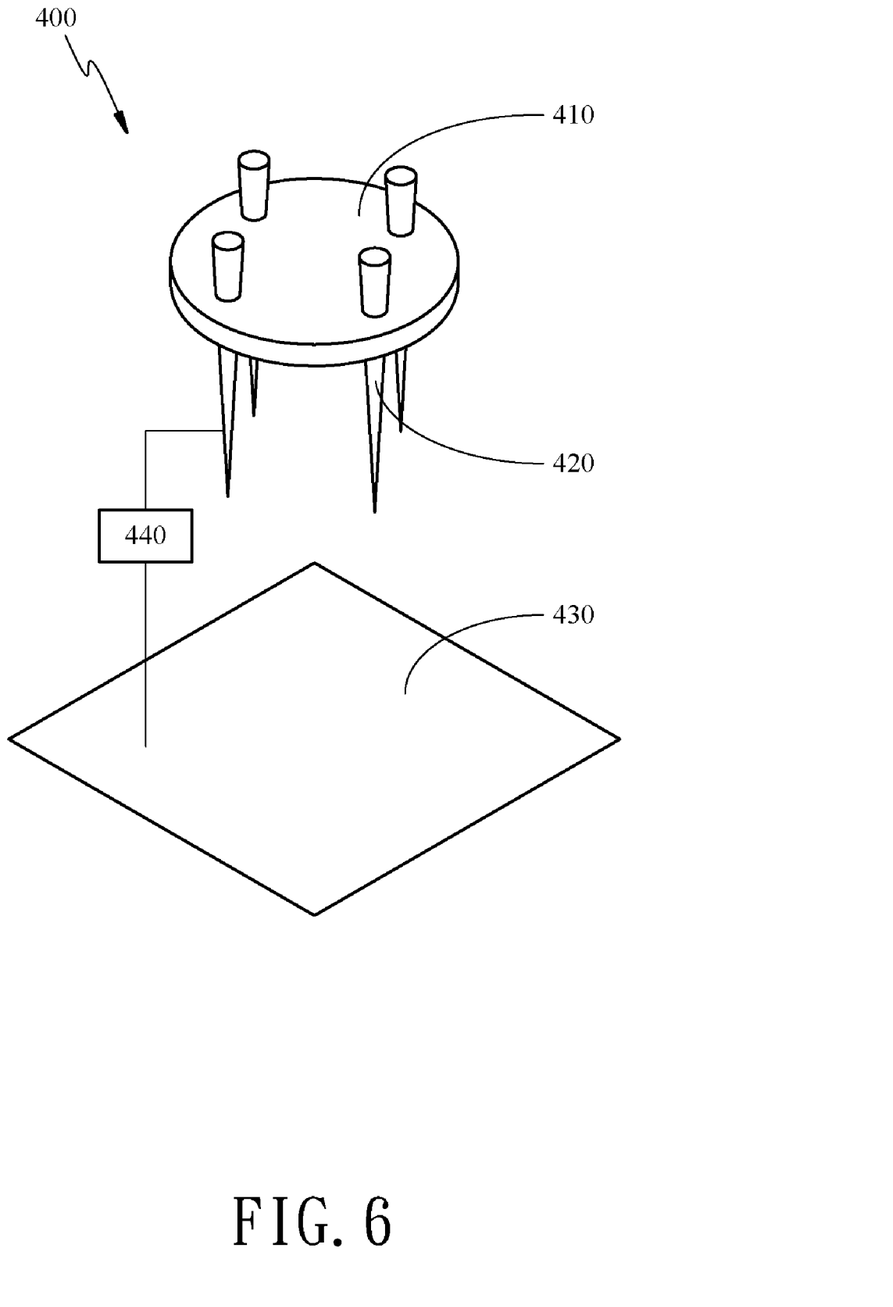
FIG. 6 shows a schematic diagram illustrating the oscillating-type blending injection device combined with a plate-type collecting device according to the present invention.

As shown in FIG. 6, the oscillating-type blending injection device combined with a plate-type collecting device 400 comprises: an oscillating-type blending injection device 410, a needle 420, a plate-type collecting device 430, and a high voltage supplying device and other auxiliary devices 440.

Obviously many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:

1. A method for forming a porous bio-mimicking scaffold, consisting essentially of the following order of process steps:
   providing at least two types of solutions wherein at least one of said solutions is a bio-mimicking scaffold solution comprising a bio-mimicking scaffold and at least one of said solutions is a pore forming solution comprising a pore forming material having at least one corresponding specific solvent;
   performing a filling process to fill said solutions into different needles of a blending injection device;
   applying a first electric property to said blending injection device and applying a second electric property to a collecting device wherein said first electric property is opposite to said second electric property, a potential difference exists between said blending injection device and said collecting device, the distance between said blending injection device and said collecting device is defined as an electric field distance, and said electric field distance divided by said potential difference is electric field intensity;
   performing an electrospinning process to have said solutions emitted from said needles of said blending injection device toward said collecting device so as to form a composite material on said collecting device wherein said composite material comprises both nanometer and micrometer scales of fibers, particles or combination of fibers and particles;
   performing a crosslinking process using a crosslinking reagent to have said bio-mimicking scaffold material undergo crosslinking, wherein said crosslinking reagent is selected from the group consisting of the following or any combination thereof: glutaraldehyde and formaldehyde; and,
   performing a removing process by using said solvent to dissolve said pore forming material to remove said pore forming material to thereby form a porous bio-mimicking scaffold;
   wherein said pore forming material is selected from the group consisting of the following or any combination thereof: chitosan, poly lactic acid, poly caprolactone-colactic acid, collagen, polyamide, and gelatin; two type of pores, one having a nanometer-scaled pore diameter and the other having a micrometer-scaled pore diameter, are formed; and said solvent in the removing process is selected from the group consisting of the following or any combination thereof: acetone and 1,4-dioxane.

2. The method according to claim 1, wherein said blending injection device further comprises an injection flow controller to control the flow within about 0.1~10 ml/hr.

3. The method according to claim 1, wherein said blending injection device is a spinning-type blending injection device further comprising a spinning speed controller to control the flow within, and the rotation speed of the blending injection device is about 100~40,000 rpm.

4. The method according to claim 1, wherein said blending injection device is an oscillating-type blending injection device further comprising an oscillating speed controller to control the flow within about 100~4,000 mm/min.

5. The method according to claim 1, wherein said collecting device is a roller-type collecting device further comprising a roller collecting speed controller to control the collecting speed within about 0~10,000 rpm.

6. The method according to claim 1, wherein said collecting device is a plate-type collecting device further comprising a plate collecting controller to control the collecting speed within about 0~1,000 mm/min.

7. The method according to claim 1, wherein said solutions are simultaneously emitted from different needles of said blending injection device toward said collecting device.

8. The method according to claim 1, wherein said solutions are repeatedly emitted from different needles of said blending injection device toward said collecting device according to a specific order or sequentially.

9. The method according to claim 1, wherein the diameter of said particle is about 1,000 nm-200,000 nm.

10. The method according to claim 1, wherein the diameter of said fiber is about 10 nm-2,000 nm.

11. The method according to claim 1, wherein said porous bio-mimicking scaffold has a pore diameter within about 1,000 nm~200,000 nm.

12. The method according to claim 1, wherein the type of each material included in said composite material is related to the concentration of the corresponding solution and, in said bio-mimicking scaffold solution, the higher is the content of said bio-mimicking scaffold, the type of the formed material via the electrospinning process is closer to a fiber, while the lower is the content of said bio-mimicking scaffold, the type of the formed material via the electrospinning process is closer to a particle.

13. The method according to claim 1, wherein the type of each material included in said composite material is related to the concentration of the corresponding solution and, in said pore forming solution, the higher is the content of said pore forming material, the type of the formed material via the electrospinning process is closer to a fiber, while the lower is the content of said pore forming material, the type of the formed material via the electrospinning process is closer to a particle.

14. The method according to claim 1, wherein the type of each material included in said composite material is related to said electric field intensity and, in said bio-mimicking scaffold solution, the higher is said electric field intensity, the type of the formed material via the electrospinning process is closer to a fiber, while the lower is said electric field intensity, the type of the formed material via the electrospinning process is closer to a particle.

15. The method according to claim 1, wherein the type of each material included in said composite material is related to said electric field intensity and, in said pore forming solution, the higher is said electric field intensity, the type of the formed material via the electrospinning process is closer to a fiber, while the lower is said electric field intensity, the type of the formed material via the electrospinning process is closer to a particle.

16. The method according to claim 1, wherein said bio-mimicking scaffold is selected from the group consisting of the following or any combination thereof: chitosan, poly lactic acid, poly caprolactone-co-lactic acid, collagen, polyamide, and gelatin.

* * * * *